(12) United States Patent
Shinto et al.

(10) Patent No.: US 8,486,997 B2
(45) Date of Patent: Jul. 16, 2013

(54) EXTERNAL PREPARATION FOR SKIN

(75) Inventors: Keisuke Shinto, Yokohama (JP); Takayuki Sakiguchi, Yokohama (JP); Kazuhiko Fujiwara, Yokohama (JP)

(73) Assignee: Shiseido Company, Chuo-ku, Tokyo (JP)

( * ) Notice: Subject to any disclaimer, the term of this patent is extended or adjusted under 35 U.S.C. 154(b) by 0 days.

(21) Appl. No.: 12/994,883

(22) PCT Filed: May 29, 2009

(86) PCT No.: PCT/JP2009/059870
§ 371 (c)(1),
(2), (4) Date: May 16, 2011

(87) PCT Pub. No.: WO2009/145300
PCT Pub. Date: Dec. 3, 2009

(65) Prior Publication Data
US 2011/0213030 A1    Sep. 1, 2011

(30) Foreign Application Priority Data

May 29, 2008   (JP) ................................. 2008-141738

(51) Int. Cl.
 *A01N 43/08*   (2006.01)
 *A01N 31/08*   (2006.01)
 *A61K 31/34*   (2006.01)
 *A61K 31/05*   (2006.01)

(52) U.S. Cl.
 USPC .......................................... 514/474; 514/734

(58) Field of Classification Search
 None
 See application file for complete search history.

(56) References Cited

U.S. PATENT DOCUMENTS

| | | | | |
|---|---|---|---|---|
| 4,959,393 | A | * | 9/1990 | Torihara et al. ............... 514/724 |
| 5,874,463 | A | * | 2/1999 | Ancira ........................... 514/460 |
| 2007/0105947 | A1 | * | 5/2007 | Tada et al. ..................... 514/456 |
| 2008/0124367 | A1 | * | 5/2008 | Yoshida et al. ............... 424/401 |

OTHER PUBLICATIONS

International Search Report for corresponding PCT/JP2009/059870 mailed Aug. 11, 2009, three pages.

* cited by examiner

*Primary Examiner* — James D Anderson
*Assistant Examiner* — Stephanie Springer
(74) *Attorney, Agent, or Firm* — Rankin, Hill & Clark LLP

(57) ABSTRACT

An external preparation for skin containing an alkylresorcinol and being excellent in temperature stability (especially high-temperature stability) and photostability. More particularly an external preparation for skin comprising (a) from 0.01 to 5% by mass of 4-isobutyl resorcinol or a salt thereof, and (b) from 0.01 to 5% by mass of one or more selected from L-ascorbic acid or a salt thereof and a 3-O-alkyl-L-ascorbic acid or a salt thereof. If desired, (c) one or more compounds selected from (c-1) a sterol skeleton-having compound (e.g., POE phytosterols, POE cholestanols), (c-2) a vitamin E derivative, (c-3) a compound such as polyglycerin fatty acid esters, polyoxybutene-polyglycerin alkyl ethers, sucrose fatty acid esters, and (c-4) a sorbitan skeleton-having compound may be incorporated in the preparation.

2 Claims, No Drawings

EXTERNAL PREPARATION FOR SKIN

TECHNICAL FIELD

The present invention relates to an external preparation for skin. More precisely, the invention relates to an external preparation for skin which contains an alkylresorcinol and has excellent temperature stability (particularly high-temperature stability) and photostability.

BACKGROUND ART

Alkylresorcinols are known to have a melanin production inhibitory effect and an antimicrobial effect, and are incorporated into cosmetics for the purpose of skin whitening and antimicrobial protection (e.g., see Patent References 1 and 2). In addition to the above-mentioned alkylresorcinols, there are known L-ascorbic acid and L-ascorbic acid derivatives as substances having a skin-whitening effect; and there have been proposed external preparations for skin containing an alkylresorcinol and an L-ascorbic acid (=L-ascorbic acid, L-ascorbic acid derivative). (e.g., see Patent References 3 and 4). Alkylresorcinols and L-ascorbic acids each have a problem in that they tend to become discolored due to temperature and light; however, sufficient investigations have not as yet been made for the technique of effectively preventing the discoloration of alkylresorcinols and L-ascorbic acids.

PRIOR ART REFERENCES

Patent References
  Patent Reference 1: JP 2-049715A
  Patent Reference 2: JP 4-169511A
  Patent Reference 3: JP 2004-277352A
  Patent Reference 4: JP 2005-120023A

SUMMARY OF THE INVENTION

Problems that the Invention is to Solve

An object of the present invention is to provide an external preparation for skin which contains an alkylresorcinol and an L-ascorbic acid and which has excellent temperature stability (particularly high-temperature stability) and photostability.

Means for Solving the Problems

The present inventors made intensive studies for the purpose of solving the above-mentioned problems, and found that any one alone of an alkylresorcinol and an L-ascorbic acid discolors due to temperature and light, but when an alkylresorcinol, especially 4-isobutyl resorcinol or its salt, is combined with an L-ascorbic acid compound, especially L-ascorbic acid or its salt or 3-O-alkyl-L-ascorbic acid or its salt, in a specific ratio, then the resulting combination exhibits an excellent photostability effect and temperature (high-temperature) stability effect, and have thereby completed the present invention.

Thus, the invention relates to an external preparation for skin comprising (a) from 0.01 to 5% by mass of 4-isobutyl resorcinol or a salt thereof, and (b) from 0.01 to 5% by mass of one or more selected from L-ascorbic acid or a salt thereof and a 3-O-alkyl-L-ascorbic acid or a salt thereof.

Of the above, an embodiment where component (b) is a 3-O-alkyl-L-ascorbic acid or a salt thereof is preferred.

ADVANTAGE OF THE INVENTION

According to the invention, there is provided an external preparation for skin which contains an alkylresorcinol and an L-ascorbic acid derivative and has excellent temperature stability (particularly high-temperature stability) and photostability.

MODE FOR CARRYING OUT THE INVENTION

The invention is described in detail hereinunder. In the following, "POE" indicates polyoxyethylene, and "POP" indicates polyoxypropylene.

4-Isobutyl resorcinol or its salt used in the invention as component (a) is a compound represented by the following formula (I) or its salt:

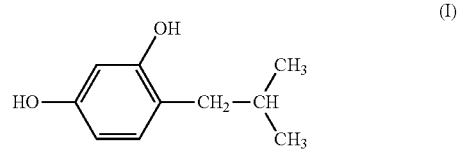

(I)

The salt of 4-isobutyl resorcinol represented by the above formula (I) includes alkali metal salts, such as sodium salt, potassium salt, and lithium salt; alkaline earth metal salts, such as magnesium salt, and calcium salt; as well as ammonium salts, and amino acid salts, but not limited thereto.

The amount of compound (a) is from 0.01 to 5% by mass in the external preparation for skin of the invention, preferably from 0.1 to 3% by mass, more preferably from 0.1 to 1% by mass. When the amount is less than 0.01% by mass, then the skin-whitening effect and the antimicrobial effect may be poor; but on the other hand, incorporation in an amount of more than 5% by mass is unfavorable in view of irritation to skin.

Component (b) to be used in the invention is one or more selected from among L-ascorbic acid or a salt thereof and a 3-O-alkyl-L-ascorbic acid or a salt thereof. The 3-O-alkyl-L-ascorbic acid or its salt includes 3-O-alkyl ethers of L-ascorbic acid, such as 3-O-methyl-L-ascorbic acid, 3-O-ethyl-L-ascorbic acid, 3-O-n-propyl-L-ascorbic acid, 3-O-isopropyl-L-ascorbic acid, 3-O-n-butyl-L-ascorbic acid, 3-O-isobutyl-L-ascorbic acid, 3-O-tert-butyl-L-ascorbic acid, 3-O-n-pentyl-L-ascorbic acid, 3-O-n-hexyl-L-ascorbic acid, 3-O-n-heptyl-L-ascorbic acid, 3-O-n-octyl-L-ascorbic acid, 3-O-n-nonyl-L-ascorbic acid, and their salts.

The said salt includes alkali metal salts, such as sodium salts, potassium salts, and lithium salts; alkaline earth metal salts, such as magnesium salts, and calcium salts; as well as ammonium salts, and amino acid salts, but not limited thereto.

In the invention, 3-o-alkyl-L-ascorbic acids or their salts are preferred; and, in particular, 3-O—$C_{1-6}$alkyl-L-ascorbic acids or their salts are most preferred.

The amount of component (b) is from 0.01 to 5% by mass in the external preparation for skin of the invention, preferably from 0.05 to 3% by mass, more preferably from 0.1 to 3% by mass. When the amount is less than 0.01% by mass, then the component could not contribute toward the temperature stability of the preparation; but on the other hand, incorporation in an amount of more than 5% by mass is unfavorable in view of irritation to skin.

In the external preparation for skin of the invention, the above component (a) and component (b) are combined, by which the preparation has excellent temperature stability (high-temperature stability) capable of effectively inhibiting the discoloration of component (a) and component (b) both, and in particular, the preparation is excellent in the effect of preventing the discoloration of the ingredients by sunlight or xenon.

In the invention, if desired, one or more compounds may be incorporated as component (c) that are selected from among (C-1) a sterol skeleton-having compound, (c-2) a vitamin E derivative, (c-3) a compound represented by the formula (II) (to be mentioned below), and (c-4) a sorbitan skeleton-having compound, from the viewpoint of the photostability. The compounds may also be in the form of their salts.

The sterol skeleton-having compound as component (c-1) includes compounds prepared through addition polymerization of phytosterols, phytostanols, cholestanols, cholesteryl ethers or the like with ethylene oxide (EO), propylene oxide (PO) or the like. The compounds may be represented by the following formula (IV):

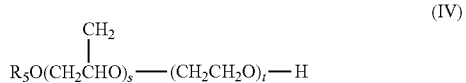

(IV)

In the formula (IV), $R_5$ represents any of a phytosterol residue, a phytostanol residue, a cholestanol residue or a cholesteryl ether residue; s indicates a number of from 0 to 100; t indicates a number of from 5 to 100.

Specific examples of the cholesterol skeleton-having compound include polyoxyethylene phytosterols, such as POE(5) phytosterol, POE(10) phytosterol, POE(20) phytosterol, POE (25) phytosterol, and POE(30) phytosterol; polyoxyethylene phytostanols, such as POE(20) phytostanol, POE(25) phytostanol, and POE (30) phytostanol; polyoxyethylene cholestanols, such as POE (20) cholestanol, POE(25) cholestanol, and POE(30) cholestanol; polyoxyethylene cholesteryl ethers, such as POE (5) cholesteryl ether, POE(10) cholesteryl ether, POE(15) cholesteryl ether, POE(20) cholesteryl ether, POE(24) cholesteryl ether, and POE(30) cholesteryl ether. Above all, preferred are POE(20) phytosterol, POE(30) phytosterol, and POE(30) cholestanol, etc., from the viewpoint of the photostability; and more preferred is POE (30) phytosterol.

As the vitamin E derivative of component (c-2), compounds are preferably used represented by the following formula (V) or (VI):

In the above formula (V) or (VI), the substituents have the following meanings. In the formulae, EO represents an ethylene oxide group, PO represents a propylene oxide group, BO represents a butylene oxide group.

$R_6$, $R_7$ and $R_8$ each independently represent a hydrogen atom or a methyl group. Preferred combinations of $R_6$, $R_7$ and $R_8$ include a case where $R_6$, $R_7$ and $R_8$ are methyl groups (5,6,7-trimethyl form, for which the starting vitamin E is α-tocopherol), a case where $R_6$ and $R_8$ are methyl groups and $R_7$ is a hydrogen atom (5,8-dimethyl form, for which the starting vitamin E is β-tocopherol), a case where $R_6$ is a hydrogen atom and $R_7$ and $R_8$ are methyl groups (7,8-dimethyl form, for which the starting vitamin E is γ-tocopherol), and a case where $R_6$ and $R_7$ are hydrogen atoms and $R_8$ is a methyl group (8-methyl form, for which the starting vitamin E is δ-tocopherol).

$R_9$ represents a hydrogen atom, an alkanoyl group having from 1 to 6 carbon atoms, an alkyl group having from 1 to 6 carbon atoms, $SO_3H$ group, $P(O)(OH)_2$ group, $CH_2COOH$ group or $COCH_2CH(SO_3H)COOH$ group.

The alkanoyl group having from 1 to 6 carbon atoms may be linear or branched, concretely including an acetyl group, a propanoyl group, a butyryl group, an isobutyryl group, and a pivaloyl group. Above all, preferred are an acetyl group, a propanoyl group, and a pivaloyl group; and more preferred is an acetyl group from the viewpoint of synthesis.

The alkyl group having from 1 to 6 carbon atoms may be linear or branched, concretely including a methyl group, an ethyl group, a propyl group, a butyl group, an isobutyl group, a t-butyl group, a pentyl group, and a hexyl group. Above all, preferred are a methyl group, an ethyl group, a propyl group, and a butyl group; and more preferred are a methyl group and an ethyl group from the viewpoint of synthesis.

$SO_3H$ group, $P(O)(OH)_2$ group, $CH_2COOH$ group or $COCH_2CH(SO_3H)COOH$ group may bond to a base to form a salt. The base is not specifically defined, so far as it has low toxicity and has no influence on the antioxidation activity and the moisture-retaining property of the vitamin E derivatives of the above formula (V) or (VI). The said salt includes alkali metal salts, such as sodium salts, potassium salts, and lithium salts; alkaline earth metal salts, such as calcium salts, and magnesium salts; metal salts, such as aluminium salts, iron salts, zinc salts, copper salts, nickel salts, and cobalt salts; inorganic salts such as ammonium salts; organic salts of

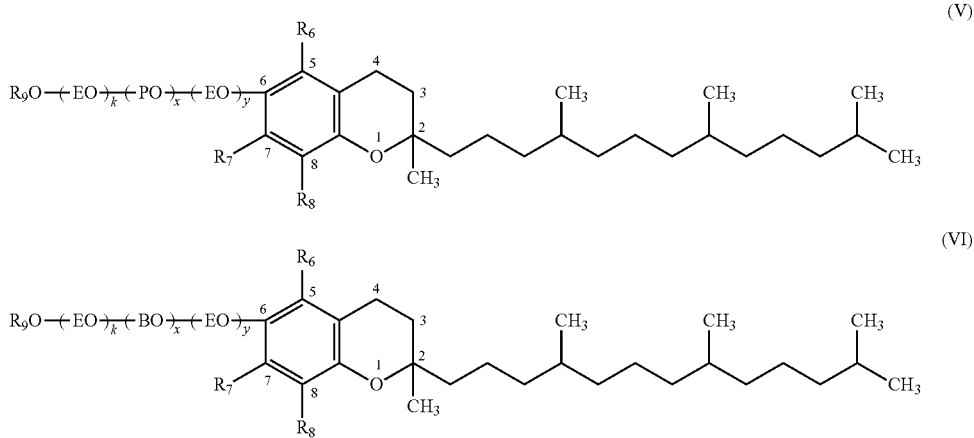

amine salts, such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts, but not limited thereto. Above all, preferred are alkali metal salts, alkaline earth metal salts, ammonium salts from the viewpoint of composition; more preferred are sodium salts, potassium salts, ½ magnesium salts, ½ calcium salts, and ammonium salts; even more preferred are sodium salts and ammonium salts.

k and y each indicate a number of from 0 to 30, preferably from 0 to 25, more preferably from 0 to 20 (with the proviso that k and y are not 0 at the same time). x indicates a number of 1 to 30, preferably from 1 to 10, more preferably from 1 to 5. Especially preferred combinations of k, x and y include a case where k and y each are from 0 to 20 (with the proviso that k and y are not 0 at the same time), and x is from 1 to 5.

Component (c-3) is a compound represented by the following formula (II):

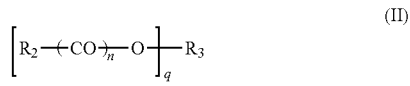

$$\left[ R_2 \!-\!\!\left(\!CO\!\right)_{\!n}\!\!-\!\!O \right]_{\!q}\!\!-\!\!R_3 \quad (II)$$

In the formula (II), $R_2$ represents a linear or branched alkyl or alkenyl group having from 12 to 22 carbon atoms.

n indicates a number of 0 or 1. q indicates an integer of from 1 to 3; when q=1, $R_3$ is a group represented by the following formula (III), or a saccharide residue; but when q=2 or 3, $R_3$ is a saccharide residue.

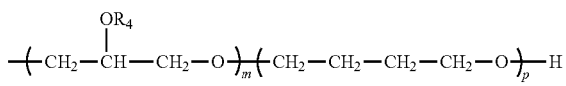

$$\!-\!\!\left(\!CH_2\!-\!\!\overset{\overset{\displaystyle OR_4}{|}}{CH}\!-\!CH_2\!-\!O\!\right)_{\!m}\!\!\left(\!CH_2\!-\!CH_2\!-\!CH_2\!-\!CH_2\!-\!O\!\right)_{\!p}\!\!-\!H \quad (III)$$

In the formula (III), $R_4$ represents a hydrogen atom, or an aliphatic acyl group having from 12 to 22 carbon atoms; m and p each independently indicate an integer of from 0 to 40, and m+p 5.

Preferred examples of the compound represented by the above formula (II) include polyglycerin fatty acid esters, polyoxybutene-polyglycerin alkyl ethers, and sucrose fatty acid esters.

A preferred polyglycerin moiety of the said polyglycerin fatty acid ester is exemplified by a 5- to 20-mer of glycerin, and that of the fatty acid moiety thereof is exemplified by lauric acid, myristic acid, palmitic acid, stearic acid, oleic acid, linolic acid, and behenic acid. That is, in the above formula (II), preferably, n=1, q=1, $R_3$ is a group represented by the formula (III) (where m is from 5 to 20, p=0), $R_2$ is a lauryl group, a myristyl group, a palmityl group, a stearyl group, an oleyl group, a linolyl group, etc. Preferred is an embodiment where the degree of esterification is from 1 to 3 per molecule on average, and the compound has at least three free hydroxyl group. Specifically, in the polyglycerin fatty acid ester represented by the formula (II), $R_3$ is a group represented by the formula (III) (this is a polyglycerin moiety where m is from 5 to 20 and p=0), from 1 to 3 of $R_4$'s in the polyglycerin moiety are aliphatic acyl groups each having from 12 to 22 carbon atoms, and at least three are hydrogens. The aliphatic acyl group having from 12 to 22 carbon atoms for $R_4$ is preferably a lauroyl group, a myristoyl group, a palmitoyl group, a stearoyl group, an oleoyl group, and a linolyol group, etc.

Many of such polyglycerin fatty acid esters are commercially available; and preferred examples thereof are decaglycerin monolaurate, decaglycerin monooleate, and decaglycerin monostearate, etc.

In the said polyoxybutene-polyglycerin alkyl ether, the addition molar number of the oxybutylene group (mean degree of polymerization) is preferably from 10 to 20 on average, and the mean addition molar number of polyglycerin (mean degree of polymerization) is preferably from 10 to 20. That is, in the formula (II), preferably, n=0, q=1, $R_3$ is a group represented by the formula (III) (where m is from 10 to 20, p is from 10 to 20), $R_2$ is a stearyl group, and an oleyl group, etc.

Some of the above-mentioned polyoxybutene-polyglycerin alkyl ethers are commercially available, and are usable here. Polyoxybutene(13)-polyglyceryl(14) stearyl ether ("Highglyol" S-26, by Nihon Surfactant Kogyo K.K.) is exemplified as preferable commercial products.

The said sucrose fatty acid ester preferably exemplified is a sucrose monofatty acid ester where n=1 and q=1, a sucrose difatty acid ester where q=2, and a sucrose trifatty acid ester where q=3. Above all, a sucrose monofatty acid ester is more preferred, in which the fatty acid moiety is preferably lauric acid, palmitic acid, stearic acid, and oleic acid. That is, in the formula (II), preferably, $R_3$ is sucrose as the saccharide residue, $R_2$ is a lauryl group, a myristyl group, a palmityl group, a stearyl group, and an oleyl group, etc. Concretely, especially preferred examples of the sucrose monofatty acid ester include sucrose monolaurate, and sucrose monostearate.

The sorbitan skeleton-having compound of component (c-4) includes sorbitan fatty acid esters, and polyoxyethylene sorbitan fatty acid esters. In these, preferred examples of the fatty acid to constitute the ester include myristic acid, palmitic acid, isostearic acid, stearic acid, and oleic acid. Above all, especially preferred is stearic acid from the viewpoint of stability enhancement. In the polyoxyethylene sorbitan fatty acid ester, the addition molar number of polyoxyethylene is preferably from 5 to 40, more preferably from 10 to 30. Specific examples of component (c-4) include polyoxyethylene (20) sorbitan monostearate [=Polysorbate 60].

In case where component (c) is incorporated, its amount is preferably from 0.01 to 7% by mass in the external preparation for skin of the invention, more preferably from 0.05 to 5% by mass, even more preferably from 0.1 to 3% by mass. When the amount is less than 0.01% by mass, then the external preparation for skin of the invention could hardly be formulated to be transparent in case where the preparation is prepared as a transparent lotion; but on the other hand, when more than 7% by mass, the preparation would be unfavorable in point of the feelings in use (increase in sticky feel) and the irritant property thereof.

The external application for skin of the invention may be prepared according to an ordinary method, containing the above-mentioned ingredients as the base thereof. In addition to the above-mentioned ingredients, the external application for skin of the invention may contain any other ingredients that are generally used in ordinary external preparations for skin, within a range not detracting the advantage of the invention. The additional ingredients include powder ingredients, liquid fats and oils, solid fats and oils, waxes, hydrocarbon oils, higher fatty acids, higher alcohols, synthetic ester oils, silicone oils, anionic surfactants, cationic surfactants, ampholytic surfactants, nonionic surfactants, humectants, water-soluble polymers, film-forming agents, UV absorbents, metal ion sequestrants, lower alcohols, polyalcohols, saccharides, amino acids, organic amines, polymer emulsions, pH regulators, skin nutrients, vitamins, antioxidants, antioxidation promoters, fragrances, and water; and these may be added to the preparation, if desired. However, the additives should not be limited to these exemplifications.

The powder ingredients include inorganic powders, such as talc, kaolin, mica, sericite, muscovite, phlogopite, synthetic mica, lepidolite, biotite, vermiculite, magnesium carbonate, calcium carbonate, aluminium silicate, barium silicate, calcium silicate, magnesium silicate, strontium silicate, metal tungstate, magnesium, silica, zeolite, barium sulfate, fired calcium sulfate (burnt plaster), calcium phosphate, fluoroapatite, hydroxyapatite, ceramic powder, metal soap (e.g., zinc myristate, calcium palmitate, aluminium stearate), and boron nitride; organic powders, such as polyamide resin powder (nylon powder), polyethylene powder, polymethyl methacrylate powder, polystyrene powder, styrene/acrylic acid copolymer resin powder, benzoguanamine resin powder, polytetrafluoroethylene powder, and cellulose powder; inorganic white pigments, such as titanium dioxide, and zinc oxide; inorganic reddish pigments, such as iron oxide (Bengal red), and iron titanate; inorganic brownish pigments such as γ-iron oxide; inorganic yellowish pigments, such as yellow iron oxide, and ocher; inorganic blackish pigments, such as black iron oxide, and low-order titanium oxide; inorganic violetish pigments, such as mango violet, and cobalt violet; inorganic greenish pigments, such as chromium oxide, chromium hydroxide, and cobalt titanate; inorganic bluish pigments, such as ultramarine, and prussian blue; pearl pigments, such as titanium oxide-coated mica, titanium oxide-coated bismuth oxychloride, titanium oxide-coated talc, colored titanium oxide-coated mica, bismuth oxychloride, and fish scale foil; metal powder pigments, such as aluminium powder, and copper powder; zirconium, barium or aluminium lake organic pigments (e.g., organic pigments, such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, etc.; as well as Red. No. 3, Red. No. 104, Red. No. 106, Red. No. 227, Red. No. 230, Red. No. 401, Red. No. 505, Orange No. 205, Yellow No. 4, Yellow No. 5, Yellow No. 202, Yellow No. 203, Green No. 3, Blue No. 1, etc.); natural colorants, such as chlorophyll, and β-carotene.

The liquid fats and oils include avocado oil, camellia oil, turtle oil, *macadamia* nut oil, corn oil, mink oil, olive oil, rapeseed oil, egg-yolk oil, sesame oil, persic oil, wheat germ oil, sasanqua oil, castor oil, linseed oil, safflower oil, cottonseed oil, *perilla* oil, soybean oil, peanut oil, tea seed oil, nutmeg oil, rice bran oil, Chinese wood oil, Japanese wood oil, jojoba oil, germ oil, and triglycerin.

The solid fats and oils include cacao butter, coconut oil, horse fat, hardened coconut oil, palm oil, beef tallow, mutton tallow, hardened beef tallow, palm kernel oil, lard, beef bone tallow, Japanese core wax, hardened oil, neatsfoot tallow, Japanese wax, and hardened castor oil.

The waxes include bees wax, candelilla wax, cotton wax, carnauba wax, bayberry wax, tree wax, whale wax, montan wax, bran wax, lanolin, kapok wax, lanolin acetate, liquid lanolin, sugarcane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

The hydrocarbon oils include liquid paraffin, ozokerite, squalane, pristane, paraffin, ceresin, squalene, vaseline, and microcrystalline wax.

The higher fatty acids include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

The higher alcohols include linear alcohols, such as lauryl alcohol, cetyl alcohol, stearyl alcohol, behenyl alcohol, myristyl alcohol, oleyl alcohol, and cetostearyl alcohol; branched alcohols, such as monostearylglycerol ether (batyl alcohol), 2-decyltetradecynol, lanolin alcohol, cholesterol, phytosterol, hexyldodecanol, isostearyl alcohol, and octyldodecanol.

The synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprylate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, tri-2-heptylundecanoic glyceride, castor oil fatty acid methyl ester, oleyl oleate, acetoglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

The silicone oils include linear polysiloxanes, such as dimethylpolysiloxane, methylphenylpolysiloxane, and diphenylpolysiloxane; cyclic polysiloxanes, such as octamethylcyclotetrasiloxane, decamethylcyclopentasiloxane, and dodecamethylcyclohexasiloxane; silicone resins forming three-dimensional networks; silicone rubbers; various modified polysiloxanes, such as amino-modified polysiloxanes, polyether-modified polysiloxanes, alkyl-modified polysiloxanes, and fluorine-modified polysiloxanes.

The anionic surfactants include fatty acid soaps, such as sodium laurate, and sodium palmitate; higher alkylsulfate salts, such as sodium laurylsulfate, and potassium lauryl sulfate; alkyl ether sulfate salts, such as triethanolamine POE-laurylsulfate, and sodium POE-laurylsulfate; n-acyl sarcosine acids, such as sodium lauroylsarcosine; higher fatty acid amide sulfonates, such as sodium N-myristoyl-N-methyltaurine, coconut oil fatty acid methyltaurid sodium salt, and laurylmethyltaurid sodium salt; phosphate salts, such as sodium POE oleyl ether phosphate, and POE stearyl ether phosphoric acid; sulfosuccinate salts, such as sodium di-2-ethylhexylsulfosuccinate, sodium monolauroylmonoethanolamide polyoxyethylene sulfosuccinate, and sodium laurylpolypropylene glycol sulfosuccinate; alkylbenzenesulfonate salts, such as sodium linear dodecylbenzenesulfonate, triethanolamine linear dodecylbenzenesulfonate, and linear dodecylbenzenesulfonic acid; higher fatty acid ester sulfate salts, such as hardened coconut oil fatty acid glycerin sulfate sodium salt; N-acylglutamate salts, such as monosodium N-lauroylglutamate, disodium N-stearoylglutamate, and monosodium N-myristoyl-L-glutamate; sulfated oils, such as turkey red oil; POE-alkyl ether carboxylic acids; POE-alkylaryl ether carboxylic acid salts; α-olefinsulfonic acid salts; higher fatty acid ester sulfonate salts; secondary alcohol sulfate salts; higher fatty acid alkylolamide sulfate salts; sodium lauroylmonoethanolamidesuccinate; ditriethanolamine N-palmitoylaspartate; and casein sodium.

The cationic surfactants include alkyltrimethyl ammonium salts, such as stearyltrimethyl ammonium chloride, and lauryltrimethyl ammonium chloride; alkylpyridinium salts, such as cetylpyridinium chloride; distearyldimethylammonium dialkyldimethylammonium chloride; poly(N,N-dimethyl-3,5-methylenepyridinium)chloride; alkyl-quaternary ammonium salts; alkyldimethylbenzylammonium salts; alkylisoquinolinium salts; dialkylmorpholinium salts; POE-alkylamines; alkylamine salts; polyamine fatty acid derivatives; amyl alcohol fatty acid derivatives; benzalkonium chloride; and benzetonium chloride.

The ampholytic surfactants include imidazoline-type ampholytic surfactants, such as 2-undecyl-N,N,N-(hydroxyethylcarboxymethyl)-2-imidazoline sodium salt, and 2-cocoyl-2-imidazaliniumhydroxide-1-carboxyethyloxy-2-sodium salt; betaine-type surfactants, such as 2-heptadecyl-N-carboxymethyl-N-hydroxyethylimidazolinium betaine, betaine lauryldimethylamino-acetate, alkyl betaine, amide betaine, and sulfobetaine.

The lipophilic nonionic surfactants include propylene glycol fatty acid esters, such as propylene glycol monostearate; and hardened castor oil derivatives.

The hydrophilic nonionic surfactants include POE-sorbitol fatty acid esters, such as POE-sorbitol monolaurate, POE-sorbitol monooleate, POE-sorbitol pentaoleate, and POE-sorbitol monostearate; POE-glycerin fatty acid esters (e.g., POE-monooleates, such as POE-glycerin monostearate, POE-glycerin monoisostearate, and POE-glycerin triisostearate); POE-fatty acid esters, such as POE-distearate, POE-monodioleate, and ethylene glycol distearate; POE-alkyl ethers, such as POE-lauryl ether, POE-oleyl ether, POE-stearyl ether, POE-behenyl ether, POE-2-octyldodecyl ether, and POE-cholestanol ether; Pluronics (e.g., Pluronic, etc.); POE/POP-alkyl ethers, such as POE/POP-cetyl ether, POE/POP-2-decyltetradecyl ether, POE/POP-monobutyl ether, POE/POP-hydrogenated lanolin, and POE/POP-glyceryl ether; tetra-POE/tetra-POP-ethylenediamine condensates, such as Tetronic; POE-castor oil/hardened castor oil derivatives, such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate; POE-bees wax/lanolin derivatives, such as POE-sorbitol bees wax; alkanolamides, such as coconut oil fatty acid diethanolamide, lauric acid monoethanolamide, and fatty acid isopropanolamide; POE-propylene glycol fatty acid esters; POE-alkylamines; POE-fatty acid amides; sucrose fatty acid esters; alkylethoxydimethylamine oxides; and trioleyl phosphate.

The humectants include polyethylene glycol, propylene glycol, glycerol, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile acid salt, dl-pyrrolidonecarboxylate salts, short-chain soluble collagen, diglycerol (EO)PO adducts, chestnut rose extract, yarrow extract, and melilot extract.

The natural water-soluble polymers include plant polymers, such as gum arabic, gum tragacanth, galactan, guar gum, carob gum, karaya gum, carrageenan, pectin, agar, quince seed (*Cyclonia oblonga*), algae colloid (brown algae extract), starch (rice, corn, potato, wheat), and glycyrrhizic acid; microbial polymers, such as xanthan gum, dextran, succinoglucane, and pullulan; animal polymers, such as collagen, casein, albumin, and gelatin.

The semi-synthetic water-soluble polymers include starch-type polymers, such as carboxymethyl starch, and methylhydroxypropyl starch; cellulose-type polymers, such as methyl cellulose, ethyl cellulose, methylhydroxypropyl cellulose, hydroxyethyl cellulose, sodium cellulose sulfate, hydroxypropyl cellulose, carboxymethyl cellulose, sodium carboxymethyl cellulose, crystalline cellulose, and cellulose powder; alginic acid-type polymers, such as sodium alginate, and propyleneglycol alginate ester.

The synthetic water-soluble polymers include vinylic polymers, such as polyvinyl alcohol, polyvinyl methyl ether, polyvinyl pyrrolidone, and carboxyvinyl polymer; polyoxyethylene-type polymers, such as polyoxyethylene-polyoxypropylene copolymers with polyethylene glycol 20,000, 40,000 or 60,000; acrylic polymers, such as sodium polyacrylate, polyethyl acrylate, and polyacrylamide; polyethyleneimine; and cationic polymers.

The inorganic water-soluble polymers include bentonite, AlMg silicate (bee gum), laponite, hectorite, and silicic anhydride.

The UV absorbents include benzoic acid-type UV absorbents, such as paraminobenzoic acid (hereinafter abbreviated as PABA), PABA monoglyceryl ester, N,N-dipropoxy-PABA ethyl ester, N,N-diethoxy-PABA ethyl ester, N,N-dimethyl-PABA ethyl ester, N,N-dimethyl-PABA butyl ester, and N,N-dimethyl-PABA ethyl ester; anthranilic acid-type UV absorbents, such as homomethyl-N-acetyl anthranilate; salicylic acid-type UV absorbents, such as amyl salicylate, menthyl salicylate, homomethyl salicylate, octyl salicylate, phenyl salicylate, benzyl salicylate, and p-isopropanolphenyl salicylate; cinnamic acid-type UV absorbents, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate(2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl-diparamethoxycinnamate; benzophenone-type UV absorbents, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl 4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; 2-phenyl-5-methylbenzoxazole; 2,2'-hydroxy-5-methylphenyl-benzotriazole; 2-(2'-hydroxy-5'-t-octylphenyl)benzotriazole; 2-(2'-hydroxy-5'-methylphenylbenzotriazole); dibenzaladine; dianisoylmethane; 4-methoxy-4'-t-butyldibenzoylmethane; and 5-(3,3-dimethyl-2-norbornylidene)-3-pentan-2-one.

The metal ion sequestrants includes 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediaminehydroxyethyltriacetate.

The lower alcohols include ethanol, propanol, isopropanol, isobutyl alcohol, and t-butyl alcohol.

The polyalcohols include dialcohols, such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol; trialcohols, such as glycerol, and trimethylolpropane; tetralcohols, such as pentaerythritol (e.g., 1,2,6-hexanetriol); pentalcohols, such as xylitol; hexylcohols, such as sorbitol, and mannitol; polyalcohol polymers, such as diethylene glycol, dipropylene glycol, triethylene glycol, polypropylene glycol, tetraethylene glycol, diglycerol, polyethylene glycol, triglycerol, tetraglycerol, and polyglycerol; dialcohol alkyl ethers, such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether; dialcohol alkyl ethers, such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether; dialcohol ether esters, such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers, such as xylyl alcohol, selachyl alcohol, and batyl alcohol; sugar alcohols, such as sorbitol, maltitol, maltotriose, mannitol, sucrose, erythritol, glucose, fructose, starch amylolysis sugar, maltose, xylitose, and alcohol prepared by reducing starch amylolysis sugar; glysolid; tetrahydrofurfuryl alcohol; POE-tetrahydrofurfuryl alcohol; POP-butyl ether; POP/POE-butyl ether; tripolyoxypropylene glycerol ether; POP-glycerol ether; POP-glycerol ether phosphoric acid; POP/POE-pentaneerythritol ether, and polyglycerol.

The monosaccharides include trioses, such as D-glyceryl aldehyde, and dihydroxy acetone; tetroses, such as D-erythrose, D-erythrulose, D-threose, and erythritol; pentoses, such as L-arabinose, D-xylose, L-lyxose, D-arabinose, D-ribose, D-ribulose, D-xylulose, and L-xylulose; hexoses, such as D-glucose, D-talose, D-psicose, D-galactose, D-fructose, L-galactose, L-mannose, and D-tagatose; heptoses, such as aldoheptose, and hepturose; octoses, such as octurose; deoxysaccharides, such as 2-deoxy-D-ribose, 6-deoxy-L-galactose, and 6-deoxy-L-mannose; aminosaccharides, such as D-glucosamine, D-galactosamine, sailic acid, aminouronic acid, and muramic acid; uronic acids, such as D-glucuronic acid, D-mannuronic acid, L-gulonic acid, D-galacturonic acid, and L-iduronic acid.

The oligosaccharides include sucrose, gunchianose, umbelliferose, lactose, planteose, isolignoses, α,α-trehalose, raffinose, lignoses, umbilicine, stachyose, and belbascose.

The polysaccharides include cellulose, quince seed, chondroitin sulfuric acid, starch, galactan, dermatan sulfate, glycogen, gum arabic, heparan sulfate, hyaluronic acid, gum tragacanth, keratan sulfate, chondroitin, xanthan gum, mucoitin sulfate, guar gum, dextran, kerato sulfate, locust bean gum, succinoglucane, and charonic acid.

The amino acids include neutral amino acids, such as threonine, and cysteine; basic amino acids, such as hydroxylysine. The amino acid derivatives include sodium acylsarcosine (sodium lauroylsarcosine), acylglutamic acid salts, sodium acyl-β-alanine, glutathione, and pyrrolidonecarboxylic acid.

The organic amines include monoethanolamine, diethanolamine, triethanolamine, morpholine, triisopropanolamine, 2-amino-2-methyl-1,3-propanediol, and 2-amino-2-methyl-1-propanol.

The polymer emulsions include acrylic resin emulsion, polyethyl acrylate emulsion, acrylic resin liquid, polyacrylalkyl ester emulsion, polyvinyl acetate resin emulsion, and natural rubber latex.

The vitamins include vitamin A, B1, B2, B6, C, E and their derivatives, pantothenic acid and its derivatives, and biotin.

The antioxidants include tocopherols, dibutylhydroxytoluene, butylhydroxyanisole, and gallic acid esters.

The antioxidation promoters include phosphoric acid, citric acid, ascorbic acid, maleic acid, malonic acid, succinic acid, fumaric acid, cephalin, hexametaphosphate, phytic acid, and ethylenediamine-tetraacetic acid.

Other ingredients that may be incorporated in the preparation of the invention are, for example, antiseptics, such as ethylparaben, and butylparaben; antiinflammatory agents, such as glycyrrhizinic acid derivatives, glycyrrhetinic acid derivatives, salicylic acid derivatives, hinokitiol, zinc oxide, and allantoin; skin-whitening agents, such as placenta extract, saxifrage extract, and arbutin; various extracts, such as *Phellodendron* bark, *Coptis japonica, Lithospermum erythrorhizon, Paeonia lactiflora, Swertia japonica*, birch, sage, loquat, ginseng, *aloe, Malva sylve*, iris, grapes, dove wheat, luffa, lily, saffron, *Cnidium officinale*, shengjiang, *Hypericum erectum, Ononis spinosa*, garlic, red pepper, tangerine peel, *Angelica acutiloba*, and seaweed; activators, such as royal jelly, photosensitive agents, and cholesterol derivatives; blood circulation promoters, such as nonylic acid vanillylamide, benzyl nicotinate, β-butoxyethyl nicotinate, capsaicin, zingerone, cantharis tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol; antiseborrheics, such as sulfur, and thiantol; antiinflammatory agents, such as tranexamic acid, and dipotassium glycyrrhizinate.

The skincare preparation of the invention may be in any form, including solubilization type one, emulsion type one, powdery dispersion type one, oil-water two-phase type one, oil-water-powder three-phase type one and others, but not limited thereto. The preparation of the invention may be in any product form, and may be used for facial skin cosmetics, such as lotions, milks, creams, facial masks and the like, as well as for body skin cosmetics and aromatizing skin cosmetics.

EXAMPLES

The present invention is hereunder described in greater detail by means of the following Examples which are by no means intended to limit the invention. Unless otherwise noted, the amounts in which various components are incorporated are indicated by % by mass relative to the system in which they are incorporated.

Example 1

Effect of 4-isobutyl resorcinol to Prevent Discoloration/Malodor of Ascorbic Acid or its Derivatives Under Irradiation with Sunlight (50° C.)

[Color Difference (ΔE), L Value]
Samples 1 to 6 shown in Table 1 below were irradiated with sunlight (50 MJ, 50° C.) After the irradiation, the samples were restored to room temperature and analyzed with a colorimeter (GretagMacbeth Color-Eye 7000A) for the color difference (ΔE). Those having a smaller color difference (ΔE) discolored less. In addition, the transparency (L value) of the samples was measured with an integrating sphere spectrophotometer (GretagMacbeth Color-Eye 7000A). Those having an L value nearer to 100 are more transparent. The results are shown in Table 1.
[Smell]
Samples 1 to 6 shown in Table 1 below were irradiated with sunlight (50 MJ, 50° C.). After the irradiation, the samples were restored to room temperature and subjected to organoleptic test by expert panelists (5 members) evaluating the smell or odor thereof. The samples were ranked in 5 stages, excellent (5 points), good (4 points), average (3 points), bad (2 points), extremely bad (1 point). The points given by the 5 panelists were averaged, and the samples were evaluated according to the following criteria.
(Evaluation)
Θ: The average point by 5 panelists is from 4.0 to 5.0.
◯: The average point by 5 panelists is from 3.0 to 3.9.
Δ: The average point by 5 panelists is from 2.0 to 2.9.
x: The average point by 5 panelists is from 1.0 to 1.9.
[Color Difference Reduction (%)]
Between the samples 1 and 2, the samples 3 and 4, and the samples 5 and 6, [{(color difference (ΔE) of the sample wherein 4-isobutyl resorcinol was not incorporated)−(color difference (ΔE) of the sample wherein 4-isobutyl resorcinol was incorporated)}/(color difference (ΔE) of the sample wherein 4-isobutyl resorcinol was not incorporated))]× 100(%) was computed. This indicates the effect of 4-isobutyl resorcinol to prevent discoloration of L-ascorbic acid or its derivative. Those of which the color difference reduction (%) is nearer to 100(%) have a more excellent discoloration-preventing effect. The results are shown in Table 1.

As obvious from the results shown in Table 1, the addition of 4-isobutyl resorcinol individually, or the addition of ascorbic acid or its derivative individually is poor in photostability and temperature (high-temperature) stability; however, by the combination of the two, it exerts a photostabilization effect and a temperature (high-temperature) stabilization effect.

Of those having a higher effect of 4-isobutyl resorcinol, the color difference reduced more (their color difference reduction was large). As a whole, 4-isobutyl resorcinol prevents discoloration of ascorbic acids; and above all, the samples 3 and 5 using 3-O-ethyl-L-ascorbic acid or L-ascorbic acid as the L-ascorbic acid ingredient had a high color difference reduction; and in particular, the sample 3 using 3-O-ethyl-L-ascorbic acid had a color difference reduction of about 97% and had a color difference of 0.091. As in these, the discoloration of 3-O-ethyl-L-ascorbic acid could be almost completely prevented by 4-isobutyl resorcinol.

Example 2

Prominenticy of Discoloration Preventing Effect of 4-isobutyl resorcinol Among alkylresorcinols

[Color Difference (ΔE), L Value]
Samples 7 to 20 shown in Table 2 below were left in a thermostat bath at 50° C. (under protection from light) for 2 weeks, then restored to room temperature, and analyzed with a colorimeter (GretagMacbeth Color-Eye 7000A) for the color difference (ΔE). Those having a smaller color difference (ΔE) discolored less. In addition, the transparency (L value) of the samples was measured with an integrating sphere spectrophotometer (GretagMacbeth Color-Eye 7000A). Those having an L value nearer to 100 are more transparent. The results are shown in Table 2.

TABLE 1

|  | Sample 1 | Sample 2 | Sample 3 | Sample 4 | Sample 5 | Sample 6 |
|---|---|---|---|---|---|---|
| Water | bal. | bal. | bal. | bal. | bal. | bal. |
| Ethanol (95%) | 5 | 5 | 5 | 5 | 5 | 5 |
| Butylene Glycol | 5 | 5 | 5 | 5 | 5 | 5 |
| Citric Acid | 0.005 | 0.005 | 0.005 | 0.005 | 0.005 | 0.005 |
| Sodium Citrate | 0.095 | 0.095 | 0.095 | 0.095 | 0.095 | 0.095 |
| 2-O-ethyl-L-ascorbic Acid | 0.1 | 0.1 | — | — | — | — |
| 3-O-ethyl-L-ascorbic Acid | — | — | 0.1 | 0.1 | — | — |
| L-ascorbic Acid | — | — | — | — | 0.1 | 0.1 |
| POE(30) Phytosterol | 0.6 | 0.6 | 0.6 | 0.6 | 0.6 | 0.6 |
| Phenoxyethanol | 0.5 | 0.5 | 0.5 | 0.5 | 0.5 | 0.5 |
| 4-Isobutyl Resorcinol | 0.25 | — | 0.25 | — | 0.25 | — |
| Color Difference (ΔE) | 2.116 | 4.785 | 0.091 | 3.079 | 0.611 | 3.406 |
| Color Difference Reduction (%) | 55.778 | | 97.044 | | 82.061 | |
| L Value | 99.428 | 97.650 | 99.825 | 98.129 | 99.711 | 98.266 |
| Smell | ◯ | x | ◯ | x | ◯ | x |
| Comprehensive Evaluation | ◯ | x | Θ | x | ◯ | x |

TABLE 2

| | Sample 7 | Sample 8 | Sample 9 | Sample 10 | Sample 11 | Sample 12 | Sample 13 | Sample 14 | Sample 15 | Sample 16 | Sample 17 | Sample 18 | Sample 19 | Sample 20 |
|---|---|---|---|---|---|---|---|---|---|---|---|---|---|---|
| Water | bal. | bal. | bal. | bal. | bal. | bal. | bal. | bal. | bal. | bal. | bal. | bal. | bal. | bal. |
| Ethanol (95%) | 5 | 5 | 5 | 5 | 5 | 5 | 5 | 5 | 5 | 5 | 5 | 5 | 5 | 5 |
| Butylene Glycol | 5 | 5 | 5 | 5 | 5 | 5 | 5 | 5 | 5 | 5 | 5 | 5 | 5 | 5 |
| Citric Acid | 0.05 | 0.05 | 0.05 | 0.05 | 0.05 | 0.05 | 0.05 | 0.05 | 0.05 | 0.05 | 0.05 | 0.05 | 0.05 | 0.05 |
| Sodium Citrate | 0.05 | 0.05 | 0.05 | 0.05 | 0.05 | 0.05 | 0.05 | 0.05 | 0.05 | 0.05 | 0.05 | 0.05 | 0.05 | 0.05 |
| 3-O-ethyl-L-ascorbic Acid | 1.0 | — | 1.0 | — | 1.0 | — | 1.0 | — | 1.0 | — | 1.0 | — | 1.0 | — |
| 4-Ethyl Resorcinol | 0.083 | 0.083 | — | — | — | — | — | — | — | — | — | — | — | — |
| 4-n-propyl Resorcinol | — | — | 0.092 | 0.092 | — | — | — | — | — | — | — | — | — | — |
| 4-Isopropyl Resorcinol | — | — | — | — | 0.092 | 0.092 | — | — | — | — | — | — | — | — |
| 4-n-butyl Resorcinol | — | — | — | — | — | — | 0.1 | 0.1 | — | — | — | — | — | — |
| 4-Isobutyl Resorcinol | — | — | — | — | — | — | — | — | 0.1 | 0.1 | — | — | — | — |
| 4-n-pentylbutyl Resorcinol | — | — | — | — | — | — | — | — | — | — | 0.108 | 0.108 | — | — |
| 4-Isopentylbutyl Resorcinol | — | — | — | — | — | — | — | — | — | — | — | — | 0.108 | 0.108 |
| Color Difference (ΔE) | 2.083 | 2.474 | 2.238 | 2.524 | 1.093 | 3.073 | 2.346 | 2.342 | 0.457 | 2.309 | 1.121 | 3.249 | 0.547 | 3.219 |
| L Value | 99.465 | 98.663 | 99.341 | 98.617 | 99.151 | 97.929 | 99.287 | 98.617 | 99.633 | 98.543 | 99.357 | 98.039 | 99.524 | 98.083 |

In Table 2, the amount of 4-isobutyl resorcinol was 0.1% by mass, and the amount of the other alkylresorcinols was so controlled as to be the equimolar amount to that of 4-isobutyl resorcinol. Since those alkylresorcinols were the subjects to be tested for discoloration, the molar number of the alkylresorcinols was made the same.

As obvious from the results in Table 2, the data of the color difference and the L value of the sample 15 that falls within the range of the invention indicate little discoloration of the sample, from which it is known that the sample exhibited the most excellent discoloration preventing effect.

Other formulation examples are shown below.

Example 3

Lotion

| (Constituent Ingredients) | (% by mass) |
|---|---|
| (1) ethanol | 5.0 |
| (2) Glycerin | 1.0 |
| (3) 1,3-Butylene glycol | 5.0 |
| (4) POE/POP decyltetradecyl ether | 0.2 |
| (5) Sodium hexametaphosphate | 0.03 |
| (6) Sodium polyaspartate | 0.1 |
| (7) 3-O-ethyl-L-ascorbic acid | 5.0 |
| (8) 4-Isobutyl resorcinol | 0.1 |
| (9) Green tea extract | 0.1 |
| (10) *Hypericum erectum* extract | 0.1 |
| (11) Peppermint extract | 0.1 |
| (12) α-glucosylhesperidin | 0.01 |
| (13) Iris root extract | 0.1 |
| (14) Trisodium EDTA | 0.1 |
| (15) Carboxyvinyl polymer | 0.05 |
| (16) Sodium acrylate/2-acrylamide-2-methylpropanesulfonic acid copolymer | 0.05 |
| (17) Potassium hydroxide | 0.02 |
| (18) Phenoxyethanol | q.s. |

-continued

| (Constituent Ingredients) | (% by mass) |
|---|---|
| (19) Pure water | bal. |
| (20) Fragrance | q.s. |

Example 4

Lotion

| (Constituent Ingredients) | (% by mass) |
|---|---|
| (1) ethanol | 10.0 |
| (2) Glycerin | 2.0 |
| (3) Dipropylene glycol | 1.0 |
| (4) Isostearic acid | 0.1 |
| (5) POE/POP methylpolysiloxane copolymer | 1.0 |
| (6) Betaine lauryldimethylaminoacetate | 0.1 |
| (7) Citric acid | 0.01 |
| (8) Sodium citrate | 0.09 |
| (9) Sodium hexametaphosphate | 0.01 |
| (10) *Chamomilla* extract | 0.1 |
| (11) *Scutellaria* root extract | 0.1 |
| (12) *Elephantopus mollis* extract | 0.1 |
| (13) 3-O-ethyl-L-ascorbic acid | 0.01 |
| (14) 4-isobutyl resorcinol | 0.01 |
| (15) Lavender oil | 0.001 |
| (16) Phenoxyethanol | q.s. |
| (17) Active hydrogen water | 1.0 |
| (18) Pure water | bal. |

Example 5

Lotion

| (Constituent Ingredients) | (% by mass) |
| --- | --- |
| (1) ethanol | 10.0 |
| (2) Glycerin | 2.0 |
| (3) Dipropylene glycol | 1.0 |
| (4) Isostearic acid | 0.1 |
| (5) POE/POP methylpolysiloxane copolymer | 1.0 |
| (6) Betaine lauryldimethylaminoacetate | 0.1 |
| (7) Citric acid | 0.01 |
| (8) Sodium citrate | 0.09 |
| (9) Sodium hexametaphosphate | 0.01 |
| (10) *Chamomilla* extract | 0.1 |
| (11) chestnut rose fruit extract | 0.1 |
| (12) *Scutellaria* root extract | 0.1 |
| (13) L-ascorbic acid | 1.0 |
| (14) 4-Isobutyl resorcinol | 1.0 |
| (15) POE(39) cholestanol | 1.0 |
| (16) Lavender oil | 0.001 |
| (17) Phenoxyethanol | q.s. |
| (18) Active hydrogen water | 1.0 |
| (19) Pure water | bal. |

Example 6

Lotion

| (Constituent Ingredients) | (% by mass) |
| --- | --- |
| (1) ethanol | 10.0 |
| (2) Glycerin | 2.0 |
| (3) Dipropylene glycol | 1.0 |
| (4) Isostearic acid | 0.1 |
| (5) POE/POP methylpolysiloxane copolymer | 1.0 |
| (6) Betaine lauryldimethylaminoacetate | 0.1 |
| (7) Citric acid | 0.09 |
| (8) Sodium citrate | 0.01 |
| (9) Sodium hexametaphosphate | 0.01 |
| (10) *Rehmanniae radix* extract | 0.1 |
| (11) *Chamomilla* extract | 0.1 |
| (12) *Scutellaria* root extract | 0.1 |
| (13) 3-O-ethyl-L-ascorbic acid | 1.0 |
| (14) 4-isobutyl resorcinol | 0.1 |
| (15) Lavender oil | 0.001 |
| (16) Phenoxyethanol | q.s. |
| (17) Active hydrogen water | 1.0 |
| (18) Pure water | bal. |

Example 7

Lotion

| (Constituent Ingredients) | (% by mass) |
| --- | --- |
| (1) ethanol | 5.0 |
| (2) Glycerin | 1.0 |
| (3) 1,3-Butylene glycol | 5.0 |
| (4) POE/POP decyltetradecyl ether | 0.2 |
| (5) Sodium hexametaphosphate | 0.03 |
| (6) Sodium polyaspartate | 0.1 |
| (7) 3-O-ethyl-L-ascorbic acid | 5.0 |
| (8) 4-Isobutyl resorcinol | 0.01 |
| (9) Green tea extract | 0.1 |
| (10) Moutan bark extract | 0.1 |
| (11) Peppermint extract | 0.1 |
| (12) α-glucosylhesperidin | 0.01 |
| (13) Iris root extract | 0.1 |
| (14) Trisodium EDTA | 0.1 |
| (15) Carboxyvinyl polymer | 0.05 |
| (16) Sodium acrylate/2-acrylamide-2-methylpropanesulfonic acid copolymer | 0.05 |
| (17) Potassium hydroxide | 0.02 |
| (18) Phenoxyethanol | q.s. |
| (19) Pure water | bal. |
| (20) Fragrance | q.s. |

Example 8

Lotion

| (Constituent Ingredients) | (% by mass) |
| --- | --- |
| (1) ethanol | 5.0 |
| (2) Glycerin | 1.0 |
| (3) 1,3-Butylene glycol | 5.0 |
| (4) POE/POP decyltetradecyl ether | 0.2 |
| (5) Sodium hexametaphosphate | 0.03 |
| (6) Sodium polyaspartate | 0.1 |
| (7) 3-O-ethyl-L-ascorbic acid | 0.01 |
| (8) 4-Isobutyl resorcinol | 1.0 |
| (9) Green tea extract | 0.1 |
| (10) *Saxifraga stolonifera* extract | 0.1 |
| (11) Peppermint extract | 0.1 |
| (12) α-glucosylhesperidin | 0.01 |
| (13) Iris root extract | 0.1 |
| (14) Trisodium EDTA | 0.1 |
| (15) Carboxyvinyl polymer | 0.05 |
| (16) Sodium acrylate/2-acrylamide-2-methylpropanesulfonic acid copolymer | 0.05 |
| (17) Potassium hydroxide | 0.02 |
| (18) Phenoxyethanol | q.s. |
| (19) Pure water | bal. |
| (20) Fragrance | q.s. |

Example 9

O/W Cream

| (Constituent Ingredients) | (% by mass) |
| --- | --- |
| (1) Liquid paraffin | 3.0 |
| (2) Vaseline | 1.0 |
| (3) Dimethylpolysiloxane | 1.0 |
| (4) Stearyl alcohol | 1.8 |
| (5) Behenyl alcohol | 1.6 |
| (6) Macadamia nut oil | 2.0 |
| (7) Hardened palm oil | 3.0 |
| (8) Squalane | 6.0 |
| (9) Stearic acid | 2.0 |
| (10) Cetyl 2-ethylhexanoate | 4.0 |
| (11) POE hardened castor oil | 0.5 |
| (12) Self-emulsifying glycerin monostearate | 3.0 |
| (13) 4-T-butyl-4'-methoxydibenzoylmethane | 0.05 |
| (14) Paraoxybenzoate ester | q.s. |
| (15) Glyceryl diparamethoxycinnamate mono-2-ethylhexanoate | 0.05 |

-continued

| (Constituent Ingredients) | (% by mass) |
|---|---|
| (16) 3-O-ethyl-L-ascorbic acid | 5.0 |
| (17) 4-Isobutyl resorcinol | 5.0 |
| (18) Sucrose stearate | 7.0 |
| (19) Potassium hydroxide | 0.15 |
| (20) Sodium hexametaphosphate | 0.05 |
| (21) Trimethylglycine | 2.0 |
| (22) Glycerin | 8.0 |
| (23) Dipropylene glycol | 5.0 |
| (24) Chinese blackberry extract | 0.1 |
| (25) Yeast extract | 0.1 |
| (26) Trisodium edetate | 0.05 |
| (27) Carboxyvinyl polymer | 0.05 |
| (28) Mica titanium | 0.1 |
| (29) Colorant | q.s. |
| (30) Pure water | bal. |

Example 10

Skin Tensioning Usage W/O Cream

| (Constituent Ingredients) | (% by mass) |
|---|---|
| (1) Dimethylpolysiloxane | 3.0 |
| (2) Decamethylcyclopentasiloxane | 13.0 |
| (3) Dodecamethylcyclohexasiloxane | 5.0 |
| (4) POE methylpolysiloxane copolymer | 1.0 |
| (5) Paraoxybenzoate ester | q.s. |
| (6) L-menthol | q.s. |
| (7) Trimethylsiloxysilicic acid | 2.0 |
| (8) Ethanol | 2.0 |
| (9) Glycerin | 3.0 |
| (10) Dipropylene glycol | 5.0 |
| (11) Polyethylene glycol 6000 | 5.0 |
| (12) 3-O-ethyl-L-ascorbic acid | 0.01 |
| (13) 4-Isobutyl resorcinol | 0.01 |
| (14) Sodium hexametaphosphate | 0.05 |
| (15) Caffeine | 0.1 |
| (16) Fennel extract | 0.1 |
| (17) Hamamelis extract | 0.1 |
| (18) Ginseng extract | 0.1 |
| (19) Trisodium edetate | 0.05 |
| (20) Dimorpholinopyridazinone | 0.01 |
| (21) Methylbis(trimethylsiloxy)silylisopentyl trimethoxycinnamate | 0.1 |
| (22) Inorganic composite powder (Cover Leaf AR-80 ™, by Shokubai Kasei Kogyo) | 5.0 |
| (23) Yellow iron oxide | q.s. |
| (24) Cobalt titanate | q.s. |
| (25) Dimethyldistearylammonium hectorite | 1.5 |
| (26) Polyvinyl alcohol | 0.1 |
| (27) Hydroxyethyl cellulose | 0.1 |
| (28) Sodium acylate/2-acrylamide-2-methylpropanesulfonic cid copolymer | 0.1 |
| (29) (Acryloyldimethyltaurine-ammonium/VP) copolymer (Aristoflex AVC ™, by Clariant) | 0.1 |
| (30) Fragrance | q.s. |
| (31) Pure water | bal. |

Example 11

O/W Emulsion

| (Constituent Ingredients) | (% by mass) |
|---|---|
| (1) Dimethylpolysiloxane | 3.0 |
| (2) Decamethylcyclopentasiloxane | 4.0 |

-continued

| (Constituent Ingredients) | (% by mass) |
|---|---|
| (3) Ethanol | 5.0 |
| (4) Glycerin | 6.0 |
| (5) 1,3-Butylene glycol | 5.0 |
| (6) Polyoxyethylene methylglucoside | 3.0 |
| (7) Sunflower oil | 1.0 |
| (8) Squalane | 2.0 |
| (9) Potassium hydroxide | 0.1 |
| (10) Sodium hexametaphosphate | 0.05 |
| (11) Hydroxypropyl-β-cyclodextrin | 0.1 |
| (12) L-ascorbic acid | 1.0 |
| (13) 4-Isobutyl resorcinol | 5.0 |
| (14) POE/POB glycol-mono-DL-α-tocopherol [Formula (VI), where $k + y = 30$ ($k = 16$, $y = 14$), $x = 2$, $R_6$, $R_7$ and $R_8$ are $CH_3$, $R_9$ is H] | 1.0 |
| (15) Dipotassium glycyrrhizinate | 0.05 |
| (16) Loquat leaf extract | 0.1 |
| (17) Sodium L-glutamate | 0.05 |
| (18) Fennel extract | 0.1 |
| (19) Lavender oil | 0.1 |
| (20) Rehmanniae radix extract | 0.1 |
| (21) Mortierella oil | 0.5 |
| (22) Sodium acetylhyaluronate | 0.1 |
| (23) Marjoram extract | 0.1 |
| (24) Dimorpholinopyridazinone | 0.1 |
| (25) Xanthane gum | 0.1 |
| (26) Carboxyvinyl polymer | 0.1 |
| (27) Acrylic acid/alkyl methacrylate copolymer (Pemulen TR-2 ™) | 0.1 |
| (28) (Acryloyldimethyltaurine-ammonium/VP) copolymer (Aristofex ACV ™, by Clariant) | 1.0 |
| (29) Red iron oxide | q.s. |
| (30) Inorganic composite powder (Cover Leaf AR-80 ™, by Shokubai Kasei Kogyo) | 1.0 |
| (31) Mica titanium | 0.1 |
| (32) Paraoxybenzoate ester | q.s. |
| (33) Pure water | bal. |

Example 12

W/O Emulsion for Daytime Use

| (Constituent Ingredients) | (% by mass) |
|---|---|
| (1) Dimethylpolysiloxane | 2.0 |
| (2) Decamethylcyclopentasiloxane | 25.0 |
| (3) Dodecamethylcyclohexasiloxane | 10.0 |
| (4) Polyoxyethylene/methylpolysiloxane copolymer | 1.5 |
| (5) Alkyl-crosslinked polymethylsiloxane/decamethylcyclopentasiloxane blend (Dow Corning 9045 Silicone Elastomer Blend ™, by Dow Corning) | 5.0 |
| (6) Trimethylsiloxysilicic acid | 1.0 |
| (7) 1,3-Butylene glycol | 5.0 |
| (8) Squalane | 0.5 |
| (9) Talc | 5.0 |
| (10) Dipotassium glycyrrhizinate | 0.1 |
| (11) Yeast extract | 0.1 |
| (12) 3-O-ethyl-L-ascorbic acid | 5.0 |
| (13) 4-Isobutyl resorcinol | 0.1 |
| (14) L-serine | 1.0 |
| (15) Akebia extract | 0.1 |
| (16) Trisodium edetate | 0.05 |
| (17) 4-T-butyl-4'-methoxydibenzoylmethane | 1.0 |
| (18) 2-Ethylhexyl paramethoxycinnamate | 5.0 |
| (19) Glyceryl diparamethoxycinnamate mono-2-ehtylhexanoate | 1.0 |
| (20) Silicone-coated titanium oxide fine particles(40 nm) | 4.0 |
| (21) Dimethyldistearylammonium hectorite | 0.5 |
| (22) Spherical polyethylene powder | 3.0 |

-continued

| (Constituent Ingredients) | (% by mass) |
|---|---|
| (23) Sodium acrylate/2-acrylamide-2-methylpropanesulfonic acid copolymer | 0.1 |
| (24) Inorganic composite powder (Cover Leaf AR-80 ™, by Shokubai Kasei Kogyo) | 1.0 |
| (25) Mica titanium | 0.1 |
| (26) Phenoxyethanol | q.s. |
| (27) Pure water | bal. |
| (28) Fragrance | q.s. |

Example 13

Pack

| (Constituent Ingredients) | (% by mass) |
|---|---|
| (1) Ethanol | 10.0 |
| (2) 1,3-Butylene glycol | 6.0 |
| (3) Polyethylene glycol 4000 | 2.0 |
| (4) Olive oil | 1.0 |
| (5) *Macadamia* nut oil | 1.0 |
| (6) Phytosteryl hydroxystearate | 0.05 |
| (7) Lactic acid | 0.05 |
| (8) Sodium lactate | 0.1 |
| (9) 3-O-ethyl-L-ascorbic acid | 0.01 |
| (10) 4-Isobutyl resorcinol | 0.01 |
| (11) POE/POP glycol-mono-DL-α-tocopherol [Formula (V), where $k + y = 30$ ($k = 16$, $y = 14$), $x = 2$, $R_6$, $R_7$ and $R_8$ are $CH_3$, $R_9$ is H] | 1.0 |
| (12) Fish collagen | 0.1 |
| (13) Molasses extract | 1.0 |
| (14) Sodium chondroitin-sulfate | 0.1 |
| (15) Yeast extract | 3.0 |
| (16) Sodium caboxymethyl cellulose | 0.2 |
| (17) Polyvinyl alcohol | 12.0 |
| (18) (Acryloyldimethyltaurine-ammonium/VP) copolymer (Aristofex AVC ™, by Clariant Corp.) | 2.0 |
| (19) Sodium acrylate/2-acrylamide-2-methylpropanesulfonic acid copolymer | 0.1 |
| (20) Alkyl-crosslinked polymethylsiloxane/dimethylpolysiloxane blend (Dow Corning 9041 Silicone Elastomer Blend ™, by Dow Corning) | 3.0 |
| (21) Inorganic composite powder (Cover Leaf AR-80 ™, by Shokubai Kasei Kogyo) | 5.0 |
| (22) Pullulan 3-tris(trimethylsiloxy)silylpropylcarbamate | 1.0 |
| (23) Paraoxybenzoate ester | q.s. |
| (24) Pure water | bal. |
| (25) Fragrance | q.s. |

Example 14

Powdery Solid Foundation

| (Constituent Ingredients) | (% by mass) |
|---|---|
| (1) Dimethylpolysiloxane | 5.0 |
| (2) Alkyl-crosslinked polymethylsiloxane/decamethylcyclopentasiloxane blend (Dow Corning 9045 Silicone Elastomer Blend ™, by Dow Corning) | 5.0 |
| (3) Pullulan 3-tris(trimethylsiloxy)silylpropylcarbamate | 0.5 |
| (4) Isostearic acid | 0.5 |
| (5) 3-O-ethyl-L-ascorbic acid | 1.0 |
| (6) 4-Isobutyl resorcinol | 5.0 |
| (7) Sucrose stearate | 3.0 |
| (8) Diisostearyl malate | 3.0 |
| (9) Glyceryl tri-2-ethylhexanoate | 1.0 |
| (10) Sorbitan sesqui-isostearate | 1.0 |
| (11) Spherical PMMA-coated mica | 6.0 |
| (12) Prism-tone powder YR | 1.0 |
| (13) Zinc oxide fine particles | 0.5 |
| (14) Titanium oxide fine particles | 2.0 |
| (15) Synthetic bronze mica | 2.0 |
| (16) Metal soap-treated talc | 8.0 |
| (17) Spherical silicic anhydride | 5.0 |
| (18) Chestnut rose extract | 0.1 |
| (19) Yeast extract | 0.1 |
| (20) Paraoxybenzoate ester | q.s. |
| (21) Methylbis(trimethylsiloxy)silylisopentyl trimethoxycinnamate | 1.0 |
| (22) 2-Ethylhexyl paramethoxycinnamate | 3.0 |
| (23) Spherical polyalkyl acrylate powder | 6.0 |
| (24) Methylhydrogenpolysiloxane-coated talc | q.s. |
| (25) Methylhydrogenpolysiloxane-coated sericite | 5.0 |
| (26) Methylhydrogenpolysiloxane-coated titanium oxide | 15.0 |
| (27) Inorganic composite powder (Cover Leaf AR-80 ™, by Shokubai Kasei Kogyo) | 10.0 |
| (28) Mica titanium | 1.0 |
| (29) Methylhydrogenpolysiloxane-coated pigment (colorant) | 5.0 |

Example 15

Powdery Solid Foundation

| (Constituent Ingredients) | (% by mass) |
|---|---|
| (1) Ceresine | 0.5 |
| (2) Dimethylpolysiloxane | 2.0 |
| (3) Methylphenylpolysiloxane | 1.0 |
| (4) Pullulan 3-tris(trimethylsiloxy)silylpropylcarbamate | 5.0 |
| (5) Alkyl-crosslinked polymethylsiloxane/decamethylcyclopentasiloxane blend (Dow Corning 9040 Silicone Elastomer Blend ™, by Dow Corning) | 5.0 |
| (6) Squalane | 7.0 |
| (7) Squalene (vegetable) | 1.0 |
| (8) Sorbitan sesqui-isostearate | 1.0 |
| (9) Glycerol-modified silicon resin-coated fired sericite | 16.0 |
| (10) Glycerol-modified silicone resin-coated sericite | 7.0 |
| (11) Yellow iron oxide-coated mica titanium | 0.1 |
| (12) Titanium oxide fine particles | 5.0 |
| (13) Talc | 10.0 |
| (14) Titanium oxide-coated sericite | 0.1 |
| (15) Boron nitride | 2.5 |
| (16) Red iron oxide-coated mica titanium | 0.1 |
| (17) Phytosterol | 0.1 |
| (18) Ascorbyl dipalmitate | 0.1 |
| (19) 3-O-ethyl-L-ascorbic acid | 5.0 |
| (20) 4-Isobutyl resorcinol | 0.1 |
| (21) POE(30) phytosterol | 7.0 |
| (22) Yeast extract | 0.1 |
| (23) Paraoxybenzoate ester | q.s. |
| (24) 2-Ethylhexyl paramethoxycinnamate | 1.0 |
| (25) Inorganic composite powder (Cover Leaf AR-80 ™, by Shokubai Kasei Kogyo) | 10.0 |
| (26) Spherical polyalkyl acrylate powder | 8.0 |
| (27) Methylhydrogenpolysiloxane-coated mica | bal. |
| (28) Methylhydrogenpolysiloxane-coated iron oxide titanium oxide sintered product | 5.0 |
| (29) Methylhydrogenpolysiloxane-coated sericite | 5.0 |
| (30) Methylhydrogenpolysiloxane-coated titanium oxide | 4.0 |
| (31) Methylhydrogenpolysiloxane-coated flaky titanium oxide | 5.0 |

-continued

| (Constituent Ingredients) | (% by mass) |
|---|---|
| (32) Methylhydrogenpolysiloxane-coated pigment (colorant) | 5.0 |
| (33) Fragrance | bal. |

Example 16

Powdery Solid Foundation

| (Constituent Ingredients) | (% by mass) |
|---|---|
| (1) α-olefin oligomer | 3.0 |
| (2) Vaseline | 3.0 |
| (3) Pullulan 3-tris(trimethylsiloxy)silylpropylcarbamate | 5.0 |
| (4) Alkyl-crosslinked polymethylsiloxane/decamethylcyclopentasiloxane blend (Dow Corning 9040 Silicone Elastomer Blend ™, by Dow Corning) | 3.0 |
| (5) *Macadamia* nut oil | 0.1 |
| (6) Sorbitan sesqui-isostearate | 1.0 |
| (7) Alkyl-modified silicone resin-coated yellow iron oxide | 2.0 |
| (8) Alkyl-modified silicone resin-coated red iron oxide | 1.0 |
| (9) Alkyl-modified silicone resin-coated black iron oxide | 0.5 |
| (10) L-ascorbic acid | 1.0 |
| (11) 4-Isobutyl resorcinol | 0.01 |
| (12) Yellow iron oxide-coated mica titanium | 5.0 |
| (13) synthetic bronze mica | 5.0 |
| (14) Titanium oxide | 1.0 |
| (15) Zinc oxide | 1.0 |
| (16) Low-temperature fired zinc oxide | 4.0 |
| (17) Fired sericite | 10.0 |
| (18) Phlogopite | 1.0 |
| (19) Aluminium oxide | 1.0 |
| (20) Inorganic composite powder (Cover Leaf AR-80 ™, by Shokubai Kasei Kogyo) | 15.0 |
| (21) Talc | bal. |
| (22) synthetic bronze mica | 5.0 |
| (23) Crosslinked silicone powder (Trefil E-506 ™, by Toray Dow Corning Silicone) | 10.0 |
| (24) Yeast extract | 5.0 |
| (25) Paraoxybenzoate ester | q.s. |
| (26) 2-Ethylhexyl paramethoxycinnamate | 1.0 |
| (27) Calcium alginate powder | 1.0 |
| (28) Fragrance | q.s. |

Example 17

Solid Foundation

| (Constituent Ingredients) | (% by mass) |
|---|---|
| (1) α-olefin oligomer | 10.0 |
| (2) Microcrystalline wax | 0.5 |
| (3) Alkyl-crosslinked polymethylsiloxane/dimethylpolysiloxane blend (Dow Corning 9041 Silicone Elastomer Blend ™, by Dow Corning) | 3.0 |
| (4) Pullulan 3-tris(trimethylsiloxy)silylpropylcarbamate | 1.0 |
| (5) Ceresine | 5.0 |
| (6) Dimethylpolysiloxane | 15.0 |
| (7) Methylphenylpolysiloxane | 10.0 |
| (8) *Macadamia* nut oil | 0.1 |
| (9) Carnauba wax | 0.1 |
| (10) Glyceryl tri-2-ethylhexanoate | 7.0 |
| (11) Cetyl 2-ethylhexanoate | 10.0 |
| (12) Sorbitan sesqui-isostearate | 1.5 |
| (13) Mica | 0.5 |
| (14) Aluminium stearate | 1.0 |
| (15) Inorganic composite powder (Cover Leaf AR-80 ™, by Shokubai Kasei Kogyo) | 3.0 |
| (16) Crosslinked silicone powder (Trefil E-506 ™, by Toray Dow Corning Silicone) | 8.0 |
| (17) N-lauroyl-L-lysine | 0.1 |
| (18) 3-O-ethyl-L-ascorbic acid | 0.01 |
| (19) 4-Isobutyl resorcinol | 5.0 |
| (20) Yeast extract | 0.1 |
| (21) Red iron oxide | q.s. |
| (22) Yellow iron oxide | q.s. |
| (23) Calcium alginate powder | 1.0 |
| (24) Nylon powder | bal. |
| (25) Spherical silicic anhydride | 1.0 |
| (26) Titanium oxide | 1.0 |

Example 18

Emulsion Foundation

| (Constituent Ingredients) | (% by mass) |
|---|---|
| (1) Microcrystalline wax | 1.0 |
| (2) Dimethylpolysiloxane | 15.0 |
| (3) Decamethylcyclopentasiloxane | 2.0 |
| (4) Alkyl-crosslinked polymethylsiloxane/decamethylcyclopentasiloxane blend (Dow Corning 9045 Silicone Elastomer Blend ™, by Dow Corning) | 3.0 |
| (5) Pullulan 3-tris(trimethylsiloxy)silylpropylcarbamate | 0.5 |
| (6) 1,3-Butylene glycol | 6.0 |
| (7) Candelilla wax | 3.0 |
| (8) Isostearic acid | 1.0 |
| (9) 3-O-ethyl-L-ascorbic acid | 0.01 |
| (10) 4-Isobutyl resorcinol | 0.1 |
| (11) Polysorbate 60 | 7.0 |
| (12) Ethylene glycol fatty acid ester | 0.1 |
| (13) Lanolin fatty acid octyldodecyl ester | 0.5 |
| (14) 2-Alkyl-N-carboxymethyl-N-hydroxyethylimidazolium betaine | 4.0 |
| (15) Titanium oxide | 7.5 |
| (16) Barium sulfate | 5.0 |
| (17) Titanium oxide | 7.0 |
| (18) Talc | 3.0 |
| (19) Silicic anhydride | 4.0 |
| (20) Crosslinked silicone powder (Trefil E-506 ™, by Toray Dow Corning Silicone) | 0.1 |
| (21) Sodium metaphosphate | 0.1 |
| (22) Hydroxypropyl-β-cyclodextrin | 0.1 |
| (23) *Hamamelis* extract | 0.1 |
| (24) Chinese peony extract | 0.1 |
| (25) Sodium chondroitinsulfate | 0.1 |
| (26) Yeast extract | 0.1 |
| (27) *Catechu* extract | 0.1 |
| (28) Paraoxybenzoate ester | q.s. |
| (29) Red iron oxide | q.s. |
| (30) Yellow iron oxide | q.s. |
| (31) Black iron oxide | q.s. |
| (32) Inorganic composite powder (Cover Leaf AR-80 ™, by Shokubai Kasei Kogyo) | 1.0 |
| (33) Xanthane gum | 0.1 |
| (34) Sodium carboxymethylcellulose | 0.1 |
| (35) Sodium acrylate/2-acrylamide-2-methylpropanesulfonic acid copolymer | 0.5 |
| (36) Pure water | bal. |

Example 19

W/O Foundation

| (Constituent Ingredients) | (% by mass) |
|---|---|
| (1) Dimethylpolysiloxane | 3.0 |
| (2) Decamethylcyclopentasiloxane | 10.0 |
| (3) POE/methylpolysiloxane copolymer | 3.0 |
| (4) Dodecamethylcyclohexasiloxane | 5.0 |
| (5) Pullulan 3-tris(trimethylsiloxy)silylpropylcarbamate | 0.1 |
| (6) Alkyl-crosslinked polymethylsiloxane/decamethylcyclopentasiloxane blend (Dow Corning 9040 Silicone Elastomer Blend ™, by Dow Corning) | 5.0 |
| (7) Glycerin | 4.0 |
| (8) 1,3-Butylene glycol | 5.0 |
| (9) Palmitic acid | 0.5 |
| (10) L-ascorbic acid | 5.0 |
| (11) 4-Isobutyl resorcinol | 0.01 |
| (12) Distearyldimethylammonium chloride | 0.2 |
| (13) Metal soap-treated talc | 2.0 |
| (14) Crosslinked silicone powder (Trefil E-506 ™, by Toray Dow Corning Silicone) | 0.1 |
| (15) Red iron oxide-coated mica titanium | 0.5 |
| (16) N-lauroyl-L-lysine | 2.0 |
| (17) Sodium L-glutamate | 2.0 |
| (18) Paraoxybenzoate ester | q.s. |
| (19) Phenoxyethanol | 0.2 |
| (20) Spherical nylon powder | 1.0 |
| (21) Spherical polyalkyl acrylate powder | 3.0 |
| (22) Blackberry lily extract | 1.0 |
| (23) Yeast extract | 5.0 |
| (24) Pure water | bal. |
| (25) Inorganic composite powder (Cover Leaf AR-80 ™, by Shokubai Kasei Kogyo) | 2.0 |
| (26) Dextrin fatty acid-treated talc | 3.0 |
| (27) Dextrin fatty acid-treated titanium dioxide | 15.0 |
| (28) Dextrin fatty acid-treated yellow iron oxide | 3.0 |
| (29) Dextrin fatty acid-treated black iron oxide | 0.5 |

Example 20

O/W Foundation

| (Constituent Ingredients) | (% by mass) |
|---|---|
| (1) Dimethylpolysiloxane | 8.0 |
| (2) Alkyl-crosslinked polymethylsiloxane/decamethylcyclopentasiloxane blend (Dow Corning 9040 Silicone Elastomer Blend ™, by Dow Corning) | 20.0 |
| (3) Pullulan 3-tris(trimethylsiloxy)silylpropylcarbamate | 5.0 |
| (4) Behenyl alcohol | 0.5 |
| (5) Batyl alcohol | 0.5 |
| (6) 1,3-butylene glycol | 5.0 |
| (7) *Macadamia* nut oil | 0.1 |
| (8) Isostearic acid | 1.5 |
| (9) Stearic acid | 1.0 |
| (10) 3-O-ethyl-L-ascorbic acid | 1.0 |
| (11) 4-Isobutyl resorcinol | 5.0 |
| (12) Behenic acid | 0.5 |
| (13) Cetyl 2-ethylhexanoate | 5.0 |
| (14) Polyoxyethylene glycerin monostearate | 1.0 |
| (15) Self-emulsifying glycerin monostearate | 1.0 |
| (16) Yellow iron oxide-coated mica titanium | 2.0 |
| (17) Titanium oxide | 4.0 |
| (18) Talc | 0.5 |
| (19) Kaolin | 3.0 |
| (20) Synthetic bronze mica | 0.1 |
| (21) Crosslinked silicone powder | 0.1 |
| (22) Silicic anhydride | 5.0 |
| (23) Potassium hydroxide | 0.2 |
| (24) Triethanolamine | 0.8 |
| (25) Yeast extract | 0.1 |
| (26) Wild thyme extract | 0.1 |
| (27) Paraoxybenzoate ester | q.s. |
| (28) 2-Ethylhexyl paramethoxycinnamate | 1.0 |
| (29) Red iron oxide | q.s. |
| (30) Yellow iron oxide | q.s. |
| (31) Black iron oxide | q.s. |
| (32) Xanthan bum | 0.1 |
| (33) Sodium acrylate/2-acrylamide-2-methylpropanesulfonic acid copolymer | 1.0 |
| (34) Inorganic composite powder (Cover Leaf AR-80 ™, by Shokubai Kasei Kogyo) | 5.0 |
| (35) Bentonite | 1.0 |
| (35) Sodium carboxymethylcellulose | 0.1 |
| (37) Pure water | bal. |
| (38) Fragrance | q.s. |

Example 21

Foundation

| (Constituent Ingredients) | (% by mass) |
|---|---|
| (1) Dodecamethylcyclohexasiloxane | 15.0 |
| (2) Decamethylcyclopentasiloxane | bal. |
| (3) Pullulan 3-tris(trimethylsiloxy)silylpropylcarbamate | 5.0 |
| (4) Alkyl-crosslinked polymethylsiloxane/dimethylpolysiloxane blend (Dow Corning 9041 Silicone Elastomer Blend ™, by Dow Corning) | 30.0 |
| (5) Ethanol | 10.0 |
| (6) Isostearic acid | 0.5 |
| (7) Myristic acid-treated zinc oxide | 0.5 |
| (8) Dextrin palmitate-coated titanium oxide | 10.0 |
| (9) Dextrin palmitate-coated talc | 7.0 |
| (10) Silicone-surface-treated titanium oxide (30 nm) | 5.0 |
| (11) Crosslinked silicone powder | 1.0 |
| (12) Spherical silicic anhydride | 2.0 |
| (13) 3-O-ethyl-L-ascorbic acid | 0.01 |
| (14) 4-Isobutylbutyl resorcinol | 0.1 |
| (15) *Sophora flavescens* extract | 0.1 |
| (16) Chinese thoroughwax extract | 1.0 |
| (17) Yeast extract | 2.0 |
| (18) Inorganic composite powder (Cover Leaf AR-80 ™, by Shokubai Kasei Kogyo) | 1.0 |
| (19) 2-Ethylhexyl paramethoxycinnamate | 5.0 |
| (20) Dextrin palmitate-coated red iron oxide | q.s. |
| (21) Dextrin palmitate-coated yellow iron oxide | q.s. |
| (22) Dextrin palmitate-coated black iron oxide | q.s. |
| (23) Fragrance | q.s. |

Example 22

Makeup Base

| (Constituent Ingredients) | (% by mass) |
|---|---|
| (1) Dimethylpolysiloxane | 5.0 |
| (2) Pullulan 3-tris(trimethylsiloxy)silylpropylcarbamate | 0.1 |
| (3) Alkyl-crosslinked polymethylsiloxane/decamethylcyclopentasiloxane blend (Dow Corning 9045 Silicone Elastomer Blend ™, by Dow Corning) | 30.0 |

| (Constituent Ingredients) | (% by mass) |
|---|---|
| (4) Decamethylcyclopentasiloxane | bal. |
| (5) Ethanol | 8.0 |
| (6) Iron blue-coated mica titanium | 0.5 |
| (7) Inorganic composite powder (Cover Leaf AR-80 ™, by Shokubai Kasei Kogyo) | 5.0 |
| (8) Methylsiloxane network polymer | 5.0 |
| (9) Crosslinked silicone powder (Trefil E-506 ™, by Toray Dow Corning) | 5.0 |
| (10) Citric acid | 0.02 |
| (11) Sodium citrate | 0.08 |
| (12) 3-O-ethyl-L-ascorbic acid | 5.0 |
| (13) 4-Isobutyl resorcinol | 0.01 |
| (14) POE/POP glycol-mono-DL-α-tocopherol [Formula (V), where k + y = 30 (k = 16, y = 14), x = 2, $R_6$, $R_7$ and $R_8$ are $CH_3$, $R_9$ is H] | 0.01 |
| (15) Turmeric extract | 0.01 |
| (16) Yeast extract | 0.1 |
| (17) Pure water | 1.0 |
| (18) POE/POP methylpolysiloxane copolymer | 5.0 |

Example 23

Makeup Base

| (Constituent Ingredients) | (% by mass) |
|---|---|
| (1) Dimethylpolysiloxane | 5.0 |
| (2) Alkyl-crosslinked polymethylsiloxane/decamethylcyclopentasiloxane blend (Dow Corning 9040 Silicone Elastomer Blend ™, by Dow Corning) | 5.0 |
| (3) Pullulan 3-tris(trimethylsiloxy)silylpropylcarbamate | 5.0 |
| (4) Decamethylcyclopentasiloxane | 25.0 |
| (5) Polyoxyethylene/methylpolysiloxane copolymer | 3.0 |
| (6) Glycerin | 1.0 |
| (7) 1,3-Butylene glycol | 5.0 |
| (8) Xylitol | 0.5 |
| (9) Isostearic acid | 0.5 |
| (10) Inorganic composite powder (Cover Leaf AR-80 ™, by Shokubai Kasei Kogyo) | 10.0 |
| (11) Alkyl-modified silicone resin-coated silicic anhydride | 2.0 |
| (12) Talc | 0.5 |
| (13) L-ascorbic acid | 1.0 |
| (14) 4-Isobutyl resorcinol | 5.0 |
| (15) Aluminium stearate | 1.0 |
| (16) Red iron oxide-coated mica titanium | 0.1 |
| (17) Sodium hexametaphosphate | 0.05 |
| (18) Dipotassium glycyrrhizinate | 0.1 |
| (19) L-serine | 0.1 |
| (20) *Hypericum* extract | 0.1 |
| (21) *Rosa rouxburghii* extract | 0.1 |
| (22) *Paeonia lactiflora* extract | 0.1 |
| (23) Lysolecithin | 0.01 |
| (24) *Saxifrage* extract | 0.1 |
| (25) Yeast extract | 0.1 |
| (26) Paraoxybenzoate ester | q.s. |
| (27) Phenoxyethanol | q.s. |
| (28) Dextrin palmitate-coated yellow iron oxide | 0.1 |
| (29) Dimethyldistearylammonium hectorite | 1.0 |
| (30) Pure water | bal. |
| (31) Trimethylsiloxysilicic acid | 1.5 |
| (32) Spherical silicic anhydride | 1.0 |
| (33) Spherical polyethylene powder | 5.0 |
| (34) Fragrance | q.s. |

Industrial Applicability

Although containing an alkylresorcinol and an L-ascorbic acid compound that have heretofore been said to readily discolor by temperature or light, the external preparation for skin of the invention is excellent in temperature stability (especially high-temperature stability) and photostability.

The invention claimed is:

1. An external preparation for skin comprising (a) from 0.01 to 5% by mass of 4-isobutyl resorcinol or a salt thereof, and (b) from 0.01 to 5% by mass of one or more selected from L-ascorbic acid or a salt thereof and a 3-O-ethyl-L-ascorbic acid or a salt thereof.

2. The external preparation for skin as claimed in claim 1, wherein component (b) is a 3-O-ethyl-L-ascorbic acid or a salt thereof.

* * * * *